United States Patent
Gaster

(10) Patent No.: US 10,278,581 B2
(45) Date of Patent: May 7, 2019

(54) WIRELESS PREGNANCY MONITOR

(71) Applicant: Bloom Technologies, Inc., San Francisco, CA (US)

(72) Inventor: Richard S. Gaster, Beverly Hills, CA (US)

(73) Assignee: Bloom Technologies NV, Genk (BE)

( * ) Notice: Subject to any disclaimer, the term of this patent is extended or adjusted under 35 U.S.C. 154(b) by 263 days.

(21) Appl. No.: 14/909,739

(22) PCT Filed: Jul. 31, 2014

(86) PCT No.: PCT/US2014/049280
§ 371 (c)(1),
(2) Date: Feb. 2, 2016

(87) PCT Pub. No.: WO2015/020886
PCT Pub. Date: Feb. 12, 2015

(65) Prior Publication Data
US 2016/0157717 A1 Jun. 9, 2016

Related U.S. Application Data

(60) Provisional application No. 61/863,816, filed on Aug. 8, 2013.

(51) Int. Cl.
*A61B 5/00* (2006.01)
*A61B 5/0444* (2006.01)
(Continued)

(52) U.S. Cl.
CPC ........ *A61B 5/0011* (2013.01); *A61B 5/02411* (2013.01); *A61B 5/02416* (2013.01);
(Continued)

(58) Field of Classification Search
CPC .............. A61B 5/0011; A61B 5/02411; A61B 5/02416; A61B 5/0444; A61B 5/0488;
(Continued)

(56) References Cited

U.S. PATENT DOCUMENTS

| | | | |
|---|---|---|---|
| 5,042,503 A | * | 8/1991 | Torok ..................... A61B 5/033 600/588 |
| 5,776,073 A | | 7/1998 | Garfield et al. |

(Continued)

FOREIGN PATENT DOCUMENTS

| | | |
|---|---|---|
| CA | 2608497 A1 | 8/2006 |
| CA | 2754721 A1 | 9/2010 |

(Continued)

OTHER PUBLICATIONS

International Preliminary Report on Patentability, PCT/US2014/049280—dated Jul. 31, 2014 dated Feb. 9, 2016; 1 pg.

(Continued)

*Primary Examiner* — Michael J Carey
(74) *Attorney, Agent, or Firm* — Aurora Consulting LLC; Ashley Sloat

(57) ABSTRACT

A apparatus for automatically detecting a pregnancy status of a patient include a patch for adhering to human skin, a uterine contraction sensor, such as electromyography (EMG), coupled to the patch with at least two electrodes, and an inertial sensor for sensing fetal movement, or Fetal Heart Rate (FHR) sensor, such as Fetal EKG or a Doppler Ultrasound. An electronic circuit is coupled to the patch, the EMG sensor and the inertial sensor, and/or FHR sensor. The circuit provides an output based on a uterine contraction signal from the EMG sensor (or Doppler ultrasound) correlated in time to a fetal movement, and/or fetal heart rate. The apparatus may include a thermometer to aid in automatically providing an indication of a pregnancy complication or ovulation status of the patient, based on the output.

59 Claims, 9 Drawing Sheets

(51) Int. Cl.
  *A61B 8/02* (2006.01)
  *A61B 8/08* (2006.01)
  *A61B 5/024* (2006.01)
  *A61B 5/0492* (2006.01)
  *A61B 5/0488* (2006.01)

(52) U.S. Cl.
  CPC .......... *A61B 5/0444* (2013.01); *A61B 5/0488* (2013.01); *A61B 5/0492* (2013.01); *A61B 5/4356* (2013.01); *A61B 5/4362* (2013.01); *A61B 5/6823* (2013.01); *A61B 5/6833* (2013.01); *A61B 5/746* (2013.01); *A61B 8/02* (2013.01); *A61B 8/0866* (2013.01); *A61B 8/488* (2013.01); *A61B 5/742* (2013.01); *A61B 2560/0412* (2013.01); *A61B 2562/0219* (2013.01); *A61B 2562/06* (2013.01); *A61B 2562/164* (2013.01)

(58) Field of Classification Search
  CPC ... A61B 5/0492; A61B 5/4356; A61B 5/4362; A61B 5/6823; A61B 5/6833; A61B 5/742; A61B 5/746; A61B 8/02; A61B 8/0866; A61B 8/488; A61B 2560/0412; A61B 2562/0219; A61B 2562/06; A61B 2562/164
  USPC .......................................... 600/300, 301, 511
  See application file for complete search history.

(56) References Cited

U.S. PATENT DOCUMENTS

| | | | |
|---|---|---|---|
| 5,954,663 A | 9/1999 | Gat | |
| 6,171,263 B1* | 1/2001 | Sullivan | A61B 5/02411 600/500 |
| 6,816,744 B2 | 11/2004 | Garfield et al. | |
| 7,532,923 B1 | 5/2009 | Hayes-Gill et al. | |
| 8,116,855 B2 | 2/2012 | James et al. | |
| 8,229,550 B2 | 7/2012 | James et al. | |
| 8,255,238 B2 | 8/2012 | Powell et al. | |
| D717,674 S | 11/2014 | Vu et al. | |
| 8,880,140 B2 | 11/2014 | Hayes-Gill et al. | |
| D739,284 S | 9/2015 | Vu et al. | |
| D739,775 S | 9/2015 | Vu et al. | |
| D739,776 S | 9/2015 | Vu et al. | |
| D739,777 S | 9/2015 | Vu et al. | |
| D739,778 S | 9/2015 | Vu et al. | |
| D740,706 S | 10/2015 | Vu et al. | |
| D743,819 S | 11/2015 | Golnik et al. | |
| D752,764 S | 3/2016 | Peters | |
| 9,307,923 B2 | 4/2016 | Peters et al. | |
| 9,314,203 B2 | 4/2016 | Peters | |
| 2007/0191728 A1 | 8/2007 | Shennib | |
| 2007/0255184 A1* | 11/2007 | Shennib | A61B 5/0006 600/591 |
| 2008/0275316 A1 | 11/2008 | Fink et al. | |
| 2009/0143650 A1 | 6/2009 | Guion-Johnson et al. | |
| 2009/0192396 A1 | 7/2009 | Hayes-Gill et al. | |
| 2009/0259133 A1* | 10/2009 | Wolfberg | A61B 5/0444 600/511 |
| 2009/0299212 A1 | 12/2009 | Principe et al. | |
| 2010/0235782 A1 | 9/2010 | Powell et al. | |
| 2010/0274145 A1 | 10/2010 | Tupin, Jr. et al. | |
| 2011/0190652 A1 | 8/2011 | Fink et al. | |
| 2011/0237972 A1 | 9/2011 | Garfield et al. | |
| 2011/0251512 A1 | 10/2011 | Fink et al. | |
| 2011/0251817 A1 | 10/2011 | Burns et al. | |
| 2011/0270118 A1 | 11/2011 | Garfield et al. | |
| 2011/0306893 A1 | 12/2011 | Harrold et al. | |
| 2012/0075103 A1 | 3/2012 | Powell et al. | |
| 2012/0150010 A1 | 6/2012 | Hayes-Gill et al. | |
| 2012/0232398 A1* | 9/2012 | Roham | A61B 8/0866 600/437 |
| 2012/0265090 A1 | 10/2012 | Fink et al. | |
| 2013/0006132 A1* | 1/2013 | Brody | A61B 5/0444 600/511 |
| 2013/0030831 A1 | 1/2013 | Powell et al. | |
| 2013/0090538 A1 | 4/2013 | Garfield et al. | |
| 2013/0275152 A1 | 10/2013 | Moore et al. | |
| 2015/0004912 A1 | 1/2015 | Diamond et al. | |
| 2015/0022366 A1 | 1/2015 | Vu et al. | |
| 2016/0058363 A1 | 3/2016 | Hayes-Gill et al. | |
| 2016/0103590 A1 | 4/2016 | Vu et al. | |

FOREIGN PATENT DOCUMENTS

| | | |
|---|---|---|
| CA | 2765124 A1 | 12/2010 |
| CA | 2870560 A1 | 10/2013 |
| EP | 1220640 B1 | 5/2008 |
| EP | 1941830 | 7/2008 |
| EP | 1941832 A1 | 7/2008 |
| EP | 1680018 B1 | 11/2008 |
| EP | 2451345 A2 | 1/2011 |
| EP | 1952760 B1 | 4/2012 |
| EP | 2745774 A1 | 6/2014 |
| EP | 3011464 A1 | 12/2014 |
| EP | 2862511 A1 | 4/2015 |
| EP | 2328471 B1 | 9/2015 |
| EP | 2997892 A1 | 3/2016 |
| WO | WO 2005-110236 | 11/2005 |
| WO | 2009150440 A1 | 12/2009 |
| WO | 2010105063 A1 | 9/2010 |
| WO | 2010144413 A1 | 12/2010 |
| WO | 2011004147 A2 | 1/2011 |
| WO | 2011094609 A2 | 8/2011 |
| WO | 2011119757 A2 | 9/2011 |
| WO | 2011130291 A2 | 10/2011 |
| WO | 2011130295 A2 | 10/2011 |
| WO | 2012061827 A1 | 5/2012 |
| WO | 2012142241 A2 | 10/2012 |
| WO | 2013052612 A2 | 4/2013 |
| WO | 2013158625 A1 | 10/2013 |
| WO | 2014162135 A1 | 10/2014 |
| WO | 2014205201 A1 | 12/2014 |
| WO | 2015013163 A1 | 1/2015 |
| WO | 2015056027 A1 | 4/2015 |

OTHER PUBLICATIONS

Shulgin, V. et al. 2014. Electrohysterographic Signals Processing for Uterine Activity Detection and Characterization, IEEE XXXIV International Scientific Conference Electronics and Nanotechnology, pp. 269-272.
Horoba, K. et al. 1999, Statistical Approach to Analysis of Electrohysterographic Signal. Proceedings of the First Joint BMES/EMBS Conference, Atlanta, GA: Oct. 13-16, p. 887.
International Search Report dated Dec. 26, 2014 from PCT/US2014/049280, 4 pgs.
Written Opinion of International Search Report dated Dec. 24, 2014 from PCT/US2014/049280, 15 pgs.
Dovetail Care, "Pregnansi", SimilarWeb Ltd, 2016, 7 pages.
De Lau Hinke et al., "Towards improving uterine electrical activity modeling and electrohysterography: ultrasonic quantification of uterine movements during labor.", Nordic Federation of Societies of Obstetrics and Gynecology, Acta Obstetricia et Gynecologica Scandinavica, 2013, 1323-1326, 92 (11).
Zimmer et al., "The relationship between uterine contractions, fetal movements and fetal heart rate patterns in the active phase of labor", Elsevier Science Publishers B.V. (Biomedical Division), 1987, 89-95, 25 (2).
International Search Report dated May 6, 2016 from International Application PCT/IB2015/002194, 7 pgs.
Written Opinion of International Search Report dated May 6, 2016 from International Application PCT/IB2015/002194, 11 pgs.
Supplementary European Search Report dated Feb. 17, 2017 for EP 14834450.0, 7 pgs.

* cited by examiner

WIRELESS PREGNANCY MONITOR

CROSS-REFERENCE TO RELATED APPLICATION

The present application claims priority under 35 § 119(e) to U.S. application Ser. No. 61/863,816, filed Aug. 8, 2014, which application is incorporated by reference in its entirety. This application is a national stage application under 35 U.S.C. § 371 of International PCT application Serial No. PCT/US2014/049280 filed Jul. 31, 2014.

FIELD

The present disclosure relates to systems, apparatus and methods for monitoring of uterine contractions and fetal heart rate (FHR) during pregnancy to assess fetal health and indicate onset of labor, and related applications.

BACKGROUND

Monitoring women late in pregnancy to predict labor and delivery is a vital part of pregnancy management for the safety of both the mother and child. A common method currently used by physicians for predicting if delivery is imminent is an external tocometer. A tocometer is a non-invasive device that is wrapped around the belly of a pregnant woman like a large elastic belt and measures the frequency of uterine contractions via strain gauge pressure sensor. The tocometer is comprised of an instrument that measures pressure changes in the abdomen of the patient. As a contraction takes place, the muscles under the skin contract, and a detectable pressure change is recorded by the tocometer. Both the strength and duration of a contraction can be indirectly measured based on the change in pressure in the abdomen. One disadvantage to the tocometer is that it must be strapped around the abdomen of the patient and around the back, which makes it difficult to put on or maintain in a uniform position, and makes it susceptible to falling off as the patient moves. Every time the waist strap moves, the readings become distorted. Also, the tocometer is typically wired to a local computer to monitor the readings, tethering the patient to a confined area. In addition, once the fetus is in the lower pelvis at the end stages of delivery, the external pressure transducer does not detect accurate pressure variations and the tocometer is no longer useful.

Once the fetus has descended into the lower pelvis and is imminently ready for delivery, a second device is typically used which is inserted into the uterus. This device is known as an intrauterine pressure catheter (IUPC). The IUPC is comprised of a thin, cylindrical tube that is inserted into the uterus and measures contractions by the change in pressure in the cylindrical tube. The IUPC is capable of direct pressure measurements as the uterus is directly contracting on the device, as well as the fetus that is being delivered. The disadvantages of using an IUPC is that the measurement technique is invasive, places the patient at increased risk of infection due to an external probe placed in the uterus, and requires the patient to have her amniotic sack ruptured prior to insertion. In addition, similar to the tocometer, the patient is typically tethered to a computer.

In both the tocometer and IUPC, the patient is physically tethered to a computer in order to monitor the readings of each device. Therefore, the patients are typically restricted to a hospital setting, and home monitoring is not convenient. Smart phone applications have been developed for monitoring of uterine contractions where the user manually presses a button every time she feels a contraction, however, this is not only difficult to use, but compliance with such tools is quite poor, often rendering the data collected meaningless.

Moreover, additional technology is required to assess the health of the fetus. The health of the fetus is currently assessed via ultrasound, recording fetal heart rate tracings, examining the fetus for characteristic movement patterns, as well as other methods. However, no universal technology or technique is capable of providing the full gamut of these tests, each of which involves bulky equipment typically restricted to a hospital setting.

Notwithstanding the advantages of prior fetal monitoring techniques, there is a need for a mechanically and electronically improved, simple to operate fetal monitoring system useful for the non-professional consumer and medical professionals alike. The present disclosure fulfills this need and provides further related advantages, as described below.

SUMMARY

Methods, apparatus and systems for pregnancy-related health status monitoring using a wearable sensor device are described in detail in the detailed description, and certain aspects are summarized below. This summary and the following detailed description should be interpreted as complementary parts of an integrated disclosure, which parts may include redundant subject matter and/or supplemental subject matter. An omission in either section does not indicate priority or relative importance of any element described in the integrated application. Differences between the sections may include supplemental disclosures of alternative embodiments, additional details, or alternative descriptions of identical embodiments using different terminology, as should be apparent from the respective disclosures.

In an aspect of the present technology, a method for automatically detecting a pregnancy or pregnancy-related status of a patient may include coupling a combined electromyography (EMG)/fetal heart rate (FHR) sensor device to an abdomen of a patient, the sensor device comprising an EMG sensor and an FHR sensor coupled to an electronic circuit, producing an EMG signal from the EMG sensor correlated in time to an FHR signal from the FHR sensor, and automatically providing an indication of a pregnancy status of the patient, based on the EMG signal correlated in time to the FHR signal. Additional aspects of the method may include wirelessly transmitting the EMG signal and FHR signal to a remote device. Conversely, the method may also include receiving the pregnancy status from the remote device, and outputting the indication of the pregnancy status from at least one of a display device or a transducer in a human-perceptible form. In an aspect, one or both of the EMG sensor and the FHR sensor may be, or may include, a Doppler ultrasound sensor. Any other suitable device or sensor configured for detecting uterine contraction may be substituted for the EMG sensor. Such a device or sensor may be generally referred to as a uterine contraction monitor.

In a related aspect, the method may include processing the EMG signal correlated in time to the FHR signal using a processor located in the combined EMG/FHR sensor device, thereby obtaining the indication of the pregnancy status. In an alternative, the method may include processing the EMG signal correlated in time to the FHR signal using a processor located in a remote device, thereby obtaining the indication of the pregnancy status. For example, the method may include outputting the indication of the pregnancy status from the remote device. In an aspect, the remote device may be, or may include, at least one of a smartphone or a tablet computer.

In another aspect, the combined EMG/FHR sensor device may include an inertial sensor configured for sensing fetal movement. In such embodiments, the method may include providing the indication of the pregnancy status further based on an inertial motion signal from the inertial sensor. In an alternative aspect, the method may include providing a separate indication of the pregnancy status based on an inertial motion signal from the inertial sensor excluding at least one of the EMG signal and FHR signal.

In another aspect, the combined EMG/FHR sensor device may further include a temperature sensor, and the method may further include providing the indication of the pregnancy status further based on a temperature signal from the temperature sensor. In alternative aspects, the method may include producing the FHR signal using the FHR sensor selected from: a Doppler ultrasound probe, an optical sensor providing a photoplethysmographic signal, or a set of electrodes providing an electrocardiographic (EKG) signal.

In related aspects of the method, providing the indication of the pregnancy status may include various, more detailed aspects, for example, providing an indication of onset of labor based on an intensity, duration and rate of contractions detected by the EMG sensor. For further example, providing the indication of the pregnancy status may include providing an indication of fetal distress during labor based on a FHR detected by the FHR sensor. Providing the indication of the pregnancy status may, for further example, include providing an indication of fetal health during labor based on the EMG signal correlated in time to the FHR signal, indicating a normal status based on detecting an acceleration of FHR for a period less than a defined time threshold correlated to sensor input indicating fetal movement, indicating a normal status based on detecting an early deceleration in the FHR that occurs gradually from the onset of a contraction for a period less than a defined time threshold and that returns to a baseline FHR after the contraction, or indicating a fetal hypoxemia status based on detecting a late deceleration wherein the FHR gradually drops after onset of the contraction for a period greater than a defined time threshold and that returns to a baseline FHR after the contraction. The method may further include accompanying the indicating of the fetal hypoxemia status with a warning advising medical attention. Still further, providing the indication of the pregnancy status may include indicating an umbilical cord compression status based on detecting a variable deceleration in the FHR wherein the FHR abruptly drops at the onset of a contraction over a period less than a defined time threshold and remains depressed for a second period greater than a second defined time threshold.

In related aspects, a wearable smart sensor apparatus may be provided for performing any of the methods and aspects of the methods summarized above. An apparatus may include, for example, a processor coupled to a memory, wherein the memory holds instructions for execution by the processor to cause the apparatus to perform operations as described above. Certain aspects of such apparatus (e.g., hardware aspects) may be exemplified by equipment such a smart sensor apparatus coupled to an adhesive patch and a wireless transmitter, for communicating with a remote terminal or computer. Similarly, an article of manufacture may be provided, including a non-transitory computer-readable medium holding encoded instructions, which when executed by a processor, cause a wearable smart sensor apparatus to perform the methods and aspects of the methods as summarized above.

For example, An apparatus for automatically detecting a pregnancy status of a patient may include a patch of material having a proximal side configured for adhering to human skin and a distal side opposite to the proximal side, an EMG sensor coupled to the patch of material, the EMG sensor comprising at least two electrodes disposed towards the proximal side of the patch of material, and one or more of an inertial sensor coupled to the patch of material and configured for sensing fetal movement when the proximal side is adhered to skin of a patient, and an electronic circuit coupled to the patch of material, coupled to the EMG sensor and to the inertial sensor, and configured for providing an output based on an EMG signal from the EMG sensor correlated in time to a fetal movement signal from the inertial sensor. The electronic circuit may include a wireless transmitter and the output may include a wireless transmission of the EMG signal and fetal movement signal to a remote device. The EMG sensor and the inertial sensor may share at least a portion of a sensor circuit. The patch of material may include separate pieces, wherein each of the separate pieces includes at least one component coupled to the electronic circuit. The apparatus may be configured for convenient temporary attachment to the abdomen of the patient via a pressure sensitive, human skin compatible adhesive layer on the patch of material. The patch may be made of a pliable material.

The electronic circuit may include a wireless receiver configured for receiving a pregnancy status from the remote device based on the EMG signal and the fetal movement signal and the output further comprises a human-perceptible indication of the pregnancy status.

The apparatus may also include a temperature sensor, wherein the electronic circuit is further configured to provide the output further based on a temperature signal from the temperature sensor. The inertial sensor may be selected from: a Doppler ultrasound probe, an optical sensor providing output signal for photoplethysmography, or a set of electrodes arranged for providing an electrocardiographic (EKG) signal.

The apparatus may further include a housing or covering enclosing the electronic circuit and disposed on the distal side of the patch of material. The apparatus may include an electronic display coupled to the electronic circuit, the electronic display configured for displaying an indication of a current pregnancy status based on the EMG signal and the fetal movement signal. The apparatus may further include an audio transducer coupled to the electronic circuit, configured for providing an audible indication of a current pregnancy status based on the EMG signal and the fetal movement signal, and optionally other data.

A more complete understanding of the methods, systems and apparatus for pregnancy-related health status monitoring will be afforded to those skilled in the art, as well as a realization of additional advantages and objects thereof, by a consideration of the following detailed description. Reference will be made to the appended sheets of drawings which will first be described briefly.

BRIEF DESCRIPTION OF THE DRAWINGS

The drawings described herein are for illustrative purposes and are not intended to limit the scope of the present disclosure. Like element numerals may be used to indicate like elements appearing in one or more of the figures.

DETAILED DESCRIPTION

The present disclosure describes a wireless and non-invasive system that combines different fetal monitoring sensors in a single compact device, which can be worn anywhere in the absence of a physician and eliminate the need for bulky medical equipment. Advantageously, the device may be adhered to the patient using a removable pressure-sensitive adhesive for comfort and stability. The device may further include circuitry for wirelessly sending data recorded by the wearable device to smart phones, computers, or central servers, whereby the patient's physician, family, or others, can be warned of any vital events that take place during a woman's pregnancy. Warnings such as impending labor, fetal health, and fetal distress can all be integrated into one non-invasive, wireless, wearable device.

Figure 1A:
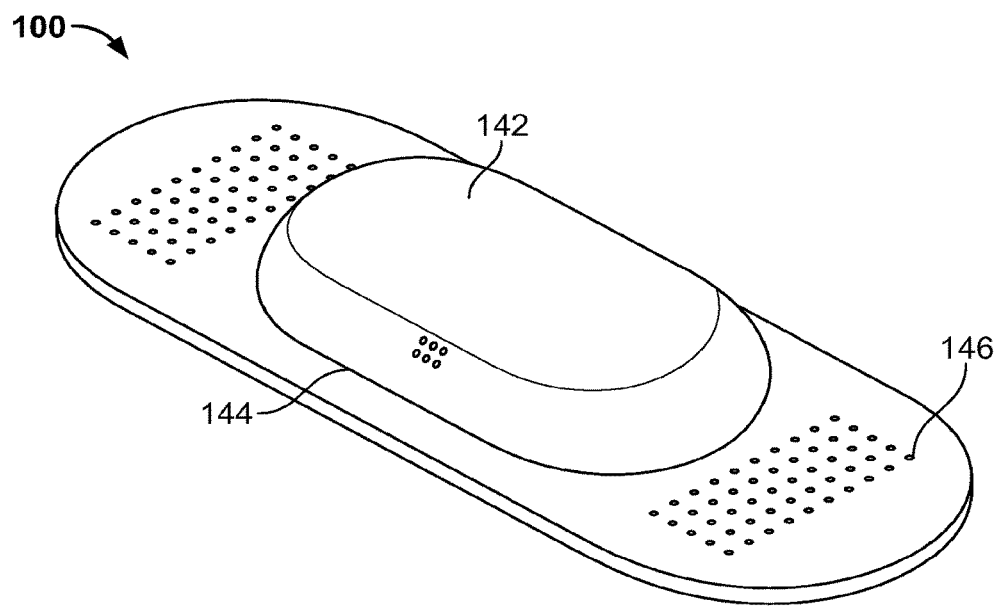
FIG. 1A is a perspective view showing an example of an apparatus using a combination of sensors on a patch and a wireless interface to detect a pregnancy status and provide an indication of the same.
Figure 1B:
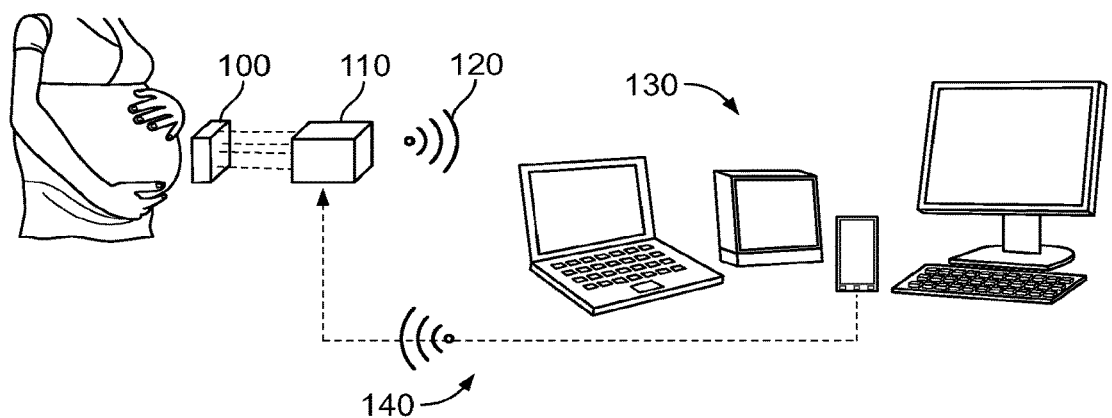
FIG. 1B is a schematic diagram of a system and apparatus for detecting and indicating a pregnancy status.
Figure 2:
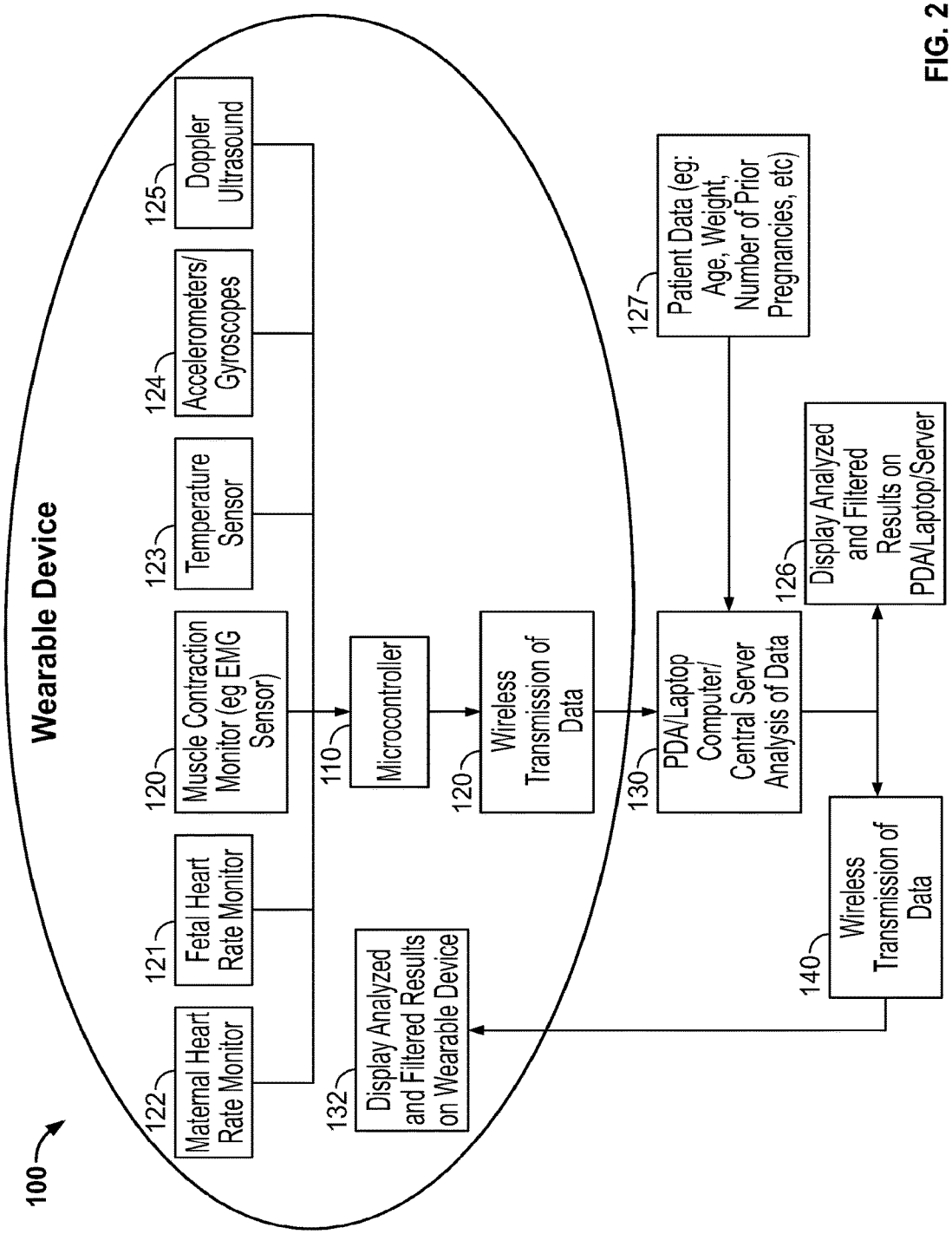
FIG. 2 is a schematic representation showing components of a wearable sensing device and related components.

Referring to FIGS. 1A-B and 2, the embodiments of this disclosure provide a wearable system for acquiring uterine EMG signals or Doppler ultrasound from a pregnant woman and measuring fetal heart rate in a single unit. The data acquired is subsequently transmitted to a remote device. A group of biosensors 100, such as an EMG sensor 120 (or other uterine contraction monitor), fetal heart rate monitor 121, maternal heart rate monitor 122, temperature sensor 123, accelerometer/gyroscope 124, Doppler ultrasound 125, and pulse oximeter among other sensors may be included in the device. For example, the combination of sensors may include any two or more of an EMG sensor, a fetal heart rate (FHR) monitor, a maternal heart rate monitor, temperature sensor, an inertial sensor such as an accelerometer or gyroscope to measure fetal movements, and/or a pulse oximeter. Specific examples of useful sensor combinations are provided later in the specification. Among other things, the sensor combination may be configured to monitor the pregnancy status, for example distinguishing between false labor and actual onset of labor, to monitor the health of the fetus before or during labor, and to monitor the health of the mother.

A microcontroller 110 and a wireless transmitter via Bluetooth, Wi-Fi, NFC, or other wireless protocol) 120 may be part of the wireless unit that is worn by the end user in the form of a pressure-sensitive adhesive patch 146 with a human skin-compatible adhesive for remote monitoring of the pregnancy. The wireless unit may include a housing 142 enclosing an electronic circuit for outputting a human-perceptible information signal 132, for example a visual display (via LEDs 144 or LCD display panel), audio (via sound alarm), or tactile feedback (via vibration or the like) based on sensor input.

The remote device 130 may be a separate device 126 that receives the raw data collected by the EMG and fetal heart rate monitor, processes the data, and provides the end user with processed and analyzed data. The separate device 126 may be remotely located and may be, or may include, a smart phone, tablet, laptop computer, central server, or the like. In an alternative embodiment, or in addition, after interpretation of data by the smartphone/remote device, the remote device may wirelessly transmit analyzed data 140 back to the wearable biosensor for display or other human-perceptible output 132 on the wearable device. In addition, vital patient information 127, for example age, date of conception, comorbidities, prior pregnancy history, or other medical data parameters may be input into the remote device in order to allow the interpretation of the data to be customized and adapted based on the patient's medical history or preferences.

In some embodiments, the wearable device may include a uterine EMG with a fetal heart tone monitor (+/−maternal heart rate monitor), enabling the correlation of uterine contraction frequency with fetal heart rate in order to provide vital diagnostic and prognostic information about the pregnancy. For example, when the fetal heart rate dips in a characteristic pattern at the time of contraction, it is indicative of the baby being in a vertex position. If, however, the fetal heart tones drop too abruptly during a contraction, that is indicative of a fetus in distress, suggesting the umbilical cord is tethered around the neck of the fetus. Therefore, the combination of EMG sensor and fetal heart tone monitor into a wireless unit will enable the user to monitor the status of her pregnancy, infer the health of her child, and be warned to go to the hospital when delivery is imminent or the fetus is in distress.

In addition, by incorporating the capability of remote transmission of data to the treating physician, the patient's treating physician may be provided access to the data of a remote patient wearing the device in real-time or near real-time for rapid analysis of sensor data collected from the patient. This rapid access to data from a remote patient may enable doctors and health care providers to provide the end user with more accurate advice on whether or not to present to the hospital, avoiding false alarms and missed alarms. An additional embodiment may include a temperature sensor in order to monitor vital signs and provide warnings to the mother that she may have an infection. For example, an elevated body temperature may indicate infection.

In addition, or in the alternative, the sensor device may be configured to receive wireless transmission of the analyzed data from the remote device back to the wearable electronic device, for example a wireless receiver or transceiver using any of the wireless technologies mentioned herein above, or other suitable wireless technology. In this way, after the data is analyzed by the remote device, the remote device may send a signal to the wearable device to display medical condition findings automatically or semi-automatically determined by the remote device. This capacity may mitigate the need to look at the remote device, for more reliable data access during stress, or for convenience. For example, with this embodiment, the end user may visualize the status of their pregnancy and fetus by looking at the wearable biosensor instead of the remote device. For example, if sensor data indicates that the fetus is doing well and labor contractions have begun, a green light may illuminate. Conversely, if sensor data indicates a risk that the baby is doing poorly, a red light may illuminate. Other possibilities for a human-perceptible interface on the wearable device may include, for example, illuminating a light or array of lights to indicate the fetal heart rate or indicate rate and/or intensity of contractions of the uterus.

In the alternative, or in addition, the wearable device or remote processing device may include a separate and custom user interface designed for a treating physician. A physician interface may organize and present the sensor data in a way that can be quickly assessed by a physician and that includes more detailed information than what may be provided to the mother in a separate end user interface. In the alternative, physician interface capabilities may be added as a distinct deeper layer or subset of a single unified interface for both patients and health providers.

In addition, or in the alternative to a fetal heart rate monitor, the wearable sensor device may include an inertial sensor, for example an accelerometer or gyroscope. Such inertial sensors may be added to the wearable electronic device to monitor not only motion of the mother, but also measure when the baby presses on the abdomen. When an acceleration event is detected by the inertial sensor, while the EMG sensor does not detect uterine or abdominal contractions, inferred processor module may infer that the acceleration is due to fetal movements.

In a related aspect, Doppler ultrasound sensing may be integrated into the wearable sensor device to record fetal motion, thereby enabling portable fetal motion monitoring. As the fetus moves, input from real-time Doppler ultrasound sensor may be used to monitor and record when the fetus is moving and when the fetus is resting. In addition, Doppler ultrasound may be designed to track fetal heart rate based on sensing the motion of the heart and/or the sound of the heart valve leaflets closing, uterine contraction based on the movement of the uterus, and fetal motion in a single integrated device. The combination of monitoring all three features in an integrated device may be used to provide diagnostic information regarding health of the fetus, automated non-stress test for the fetus, the onset and progress of labor and delivery.

Additional sensors that may be integrated into the wearable device may include a pulse oxygen sensor, enabling measurement of not only the maternal heart rate but also the blood oxygen level for monitoring the overall health of the end user both before and during delivery. A temperature sensor such as, for example, a thermistor or thermocouple, may also be integrated into the wearable device to monitor temperature of the end user. For example, a temperature sensor integrated into the wearable device may be used to monitor for ovulation timing prior to pregnancy. Such a feature may aid mothers planning to get pregnant with intercourse timing to maximize their chances of getting pregnant. Once the end user is pregnant, the same temperature sensor could be used for tracking temperature to aid in the diagnosis of infection during pregnancy, for example, to detect chorioamnionitis.

In alternative embodiments, the wearable device may include a skin stretch sensor configured to measure skin stretch during a contraction. A skin stretch sensor may include two or more terminals adhered to the belly of the end user with a sensor that detects slight distance changes between the terminals. When a contraction occurs, the surface tension of the contraction will cause the terminals to move with respect to one another. Movement of the terminals may be detected via a strain gauge, piezoelectric device, or any other device that is capable of converting a mechanical change in distance into an electrical change.

A processor in the wearable device (e.g., microcontroller 110) or in a remote device (e.g., remote device 130) may execute one or more algorithms integrated into software on the remote device and/or wearable electronic device. These algorithms may include automatic numeric processing of signal data from the wearable device, based on equations or other relationships between signal elements. Input data may include an EMG data stream (or other data stream indicative of uterine contraction) correlated in time to a FHR signal, fetal movement signal, or other sensor input. The algorithms may be designed to predict onset of labor and assess fetal and maternal health, among other things. Various examples of useful algorithms are described below.

Figure 3:
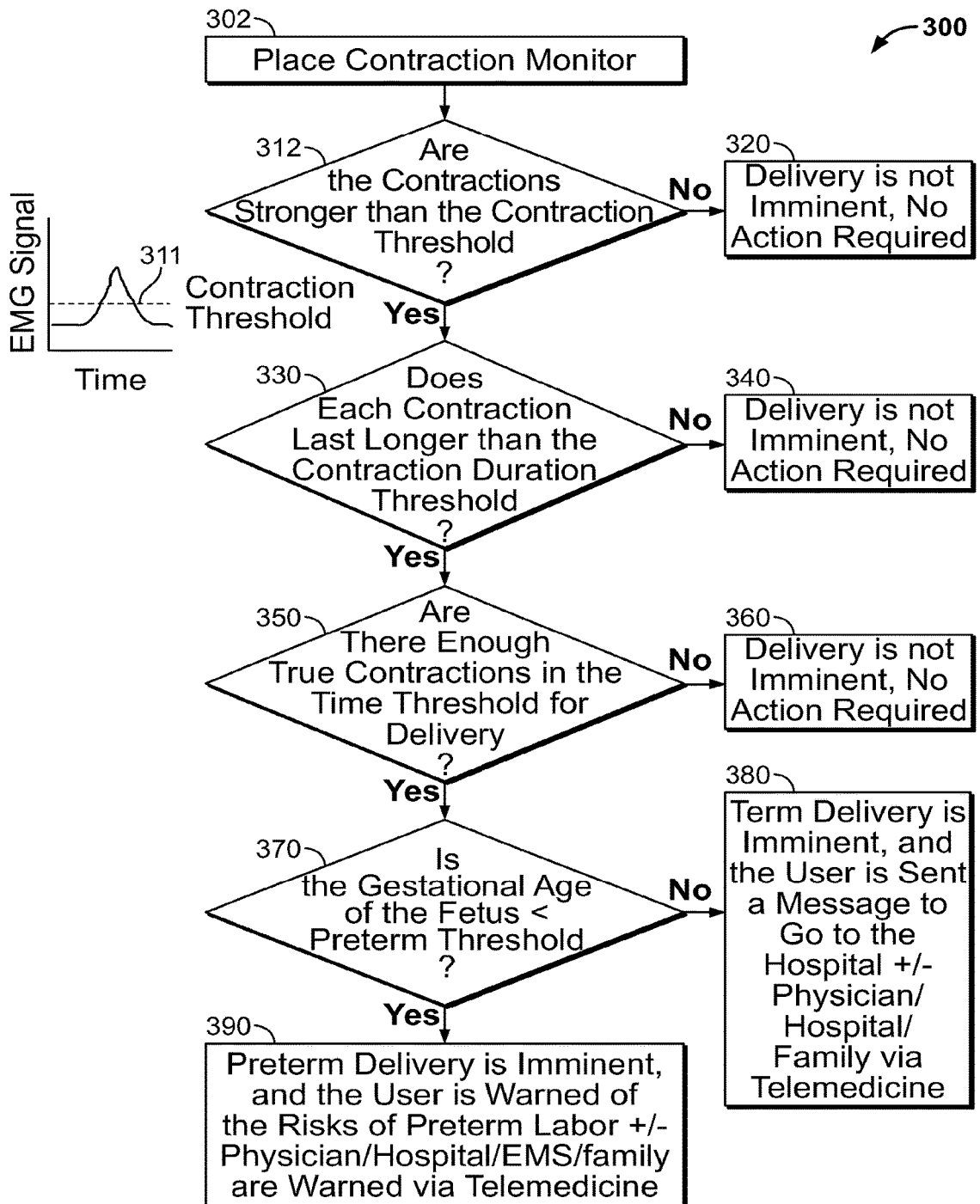
FIG. 3 is a flowchart illustrating aspects of a method for using a device to determine whether labor is imminent.

Referring to FIG. 3, a processor may perform an algorithm 300 for predicting onset of labor using the strength of contractions, duration of contractions, and rate of contractions detected by the wearable device. After the wearable device is placed on the pregnant women 302, the contraction monitor measures the strength of each contraction, for example using an EMG sensor. If the strength of each contraction, measured by the EMG contraction sensor, is less than the pre-defined "contraction threshold" 311, the contraction threshold algorithm 312 reveals that delivery is not imminent and the algorithm 300 may output an indication that no action is required.

If the strength of the contractions recorded is greater than the "Contraction Threshold" 312, then the contractions threshold algorithm 300 may determine 312 that the contractions are strong enough to support labor. In such case, the contractions may be analyzed for the duration of each contraction 330. If each contraction lasts longer than the "Contraction Duration Threshold", then the algorithm 300 may determine 330 that a state of "True Contractions" that are strong enough to support delivery exist. If each contraction does not last longer than the "Contraction Duration Threshold" then the algorithm 300 may determine 330 that contractions are not strong enough to support delivery and output an indication that delivery is not imminent 340.

Once the strength of the contractions are greater than the contraction threshold and each contraction lasts longer than the contraction duration threshold, the processor may analyze the contractions to determined whether a frequency of contractions exceeds a "Time Threshold" necessary to support delivery 350. If there are not enough true contractions occurring within the time threshold, the algorithm 300 may output an indication that delivery is not imminent 360. However, if there are enough true contractions occurring within the time delivery threshold, then the algorithm 300 may output an indication that delivery is imminent, perform further processing, or both. The number of contractions that are enough to support true delivery is referred to as the "Contraction Number Limit" and must take place within the predefined "Time Threshold".

Next, the processor may determine an age of the fetus according to the "Preterm Threshold" 370. If the gestational age of the fetus is greater than the "Preterm Threshold," then the algorithm 300 may output an indication warning the mother that term delivery is imminent 380. In addition, in the event that labor is diagnosed, the patient has the option to send a warning signal to individuals such as family, friends, treating physician, hospital, emergency medical service (EMS), as well as others via telemedicine 380.

If the gestational age of the fetus is less than the "Preterm Threshold," then the algorithm 300 may output an indication warning the mother that preterm delivery is imminent, and display the risks associated with preterm labor 390. In addition, in the event that labor is diagnosed, the patient has the option to send a warning to individuals such as family, friends, treating physician, hospital, emergency medical service (EMS), as well as others via telemedicine 390.

Figure 4:
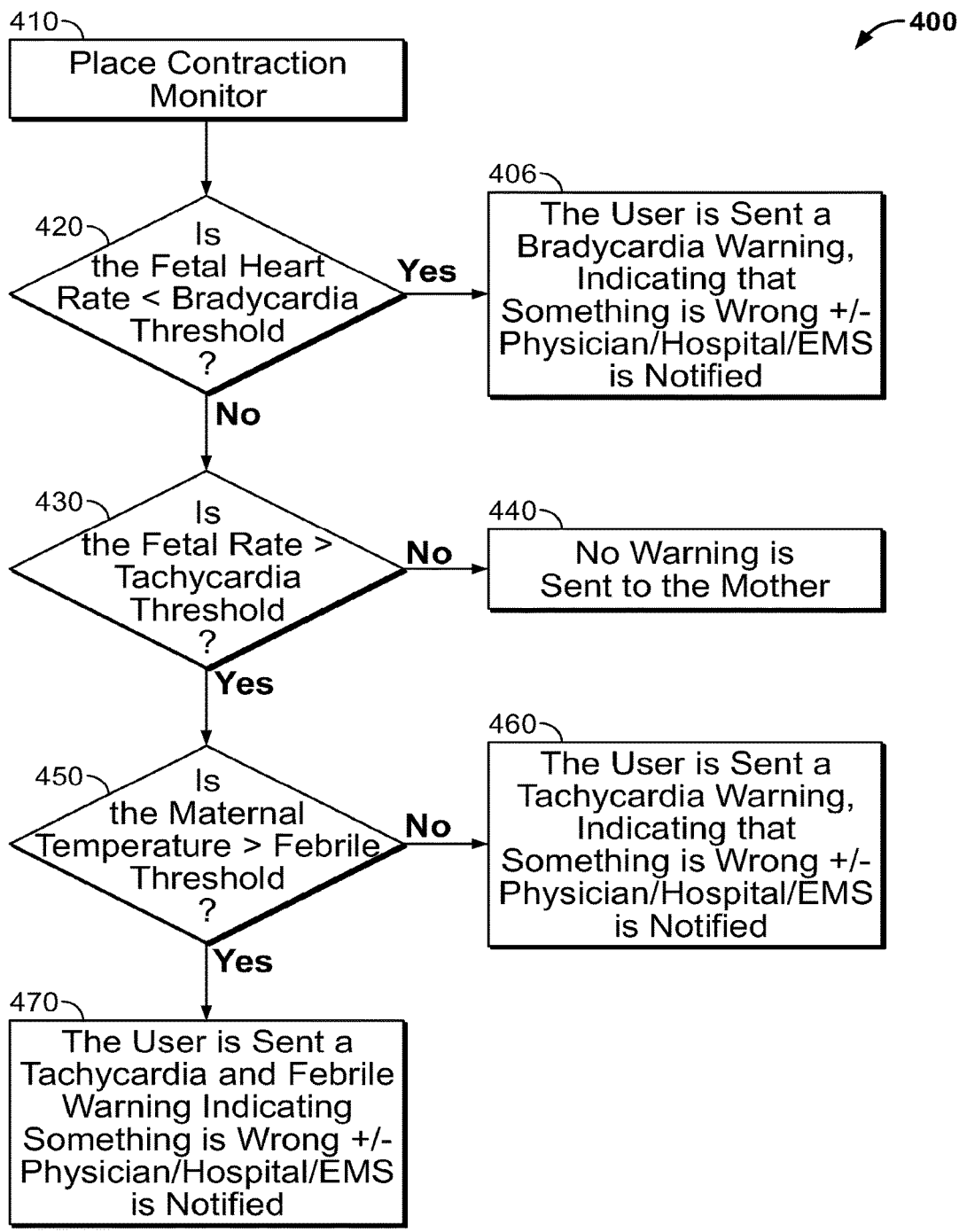
FIG. 4 is a flowchart illustrating aspects of a method for using a device to sense and indicate a health status of the fetus during labor.

For example, if an EMG or other uterine contraction monitor detects contractions that are stronger than the "Contraction Threshold" and each contraction lasts longer than 30 seconds ("The Time Threshold"), then the algorithm 300 may determine that the contractions are "True Contractions." If there are greater than or equal to, for example, 3 true contractions set as a pre-defined "Contraction Limit," in a 30 minute time period set as a pre-defined "Time Threshold," then algorithm 300 may provide a warning to the end user that she may be beginning to go into labor. If, in addition, the current gestational age is <37 weeks, the "Preterm Threshold," then preterm labor is diagnosed. And if the current gestational age is >37 weeks, then term labor is diagnosed. Of note, if the physician documents concurrent cervical changes, then positive predictive value of labor as a diagnosis is increased. Referring to FIG. 4, a processor may perform an algorithm 400 for monitoring fetal heart rate tracings correlated in time to inertial sensor data for accelerations and decelerations and/or temperature sensor data indicating patient body temperature, providing mothers with an overall indication of the health of her fetus.

First the mother may adhere the contraction monitor to her belly 410 using an adhesive patch or the like. At 420, the processor may analyze data from the fetal heart rate sensor and based on the data determines whether the fetal heart rate is less than a "Bradycardia Threshold," for example 110 beats per minute, that is diagnostic of bradycardia and is suggestive of either congenital heart malformation, or severe hypoxia due to uterine hyper-stimulation, cord prolapse, or rapid fetal descent, among others. If the sensor data indicates an FHR less than the Bradycardia Threshold, the algorithm 400 may cause a custom bradycardia warning to be displayed to the end user 406. The algorithm may further cause the monitoring device to transmit a warning message to one or more designated addresses, for example patient-designated, physician, EMR, or other destination. The Algorithm may format the message to contain information relevant an appropriate for the intended recipient. For example, a physician may receive a more technical message than provided to a patient-designated family member.

At 430, the processor may analyze the sensor data and determine whether or not the fetal heart rate is greater than a "Tachycardia Threshold," for example 160 beats per minute, which is suggestive of hypoxia, maternal fever, or anemia. If the sensor data indicates an FHR greater than the Tachycardia Threshold, the algorithm 400 may cause a custom tachycardia warning to be displayed to the end user 460. Conversely, if the FHR is less than the Tachycardia Threshold, the algorithm 400 may abstain from providing 440 a warning, or provide a "normal" indication.

At 450, the processor may analyze the sensor data and determine that the maternal temperature measured by a temperature sensor is greater than a "Febrile Threshold," for example 101 degrees Fahrenheit, and the fetal heart rate is greater that the Tachycardia Threshold, that is suggestive of an infection. If the processor detects these conditions, the algorithm 400 may cause a custom febrile warning/infection warning to be displayed to the end user 470 and/or transmitted to designated addresses.

In the event that the fetus is in distress for any of the above described reasons, the patient has the option to send a custom warning message to individuals such as the family members, treating physician, the hospital, EMS, among others via telemedicine as shown at 406 or 470.

Figure 5:
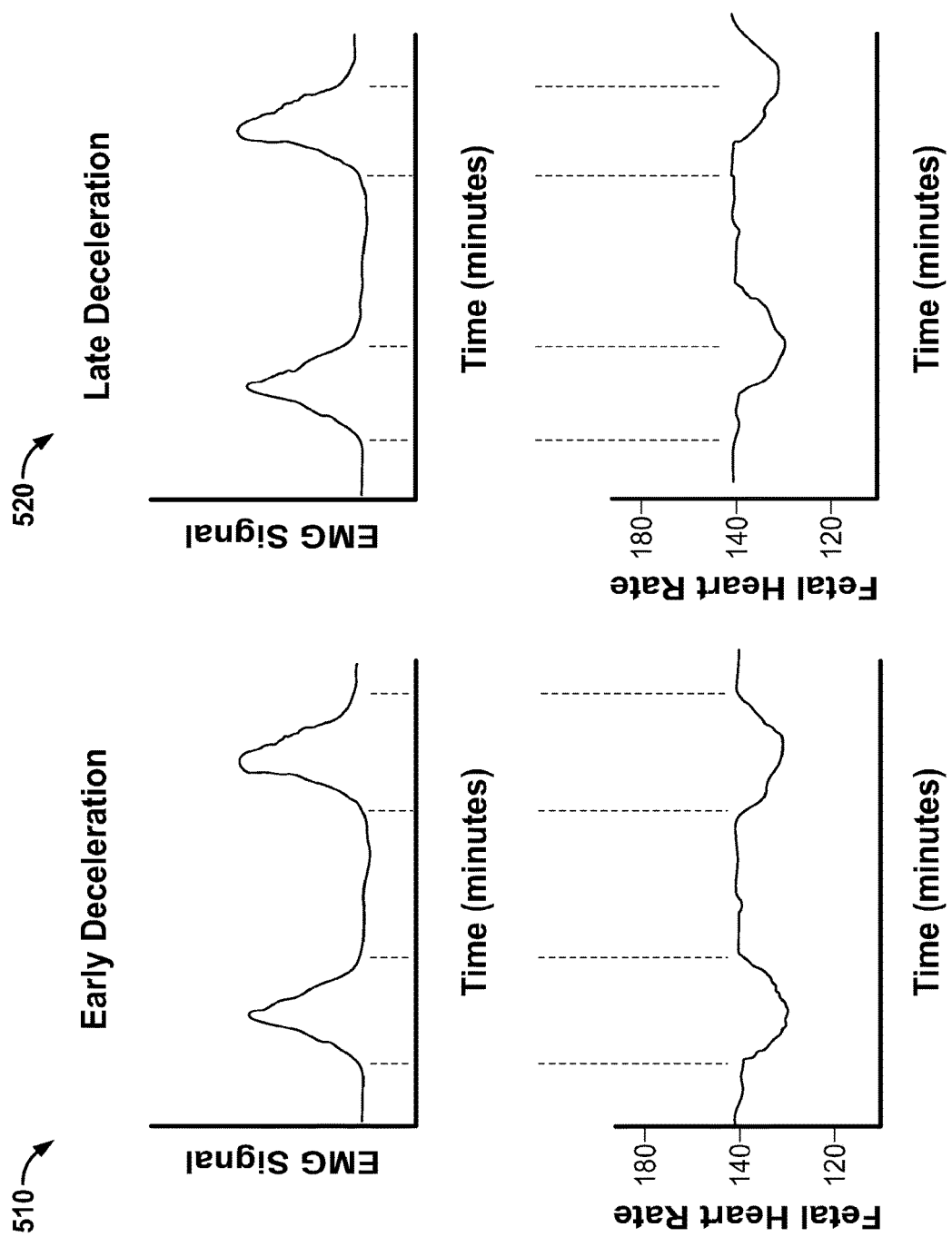
FIG. 5 is a set of graphs illustrating a time of EMG contraction correlated with changes in fetal heart rate such as may be used for diagnosis of early deceleration, late deceleration and variable deceleration, using data from a device as described herein.
Figure 5:
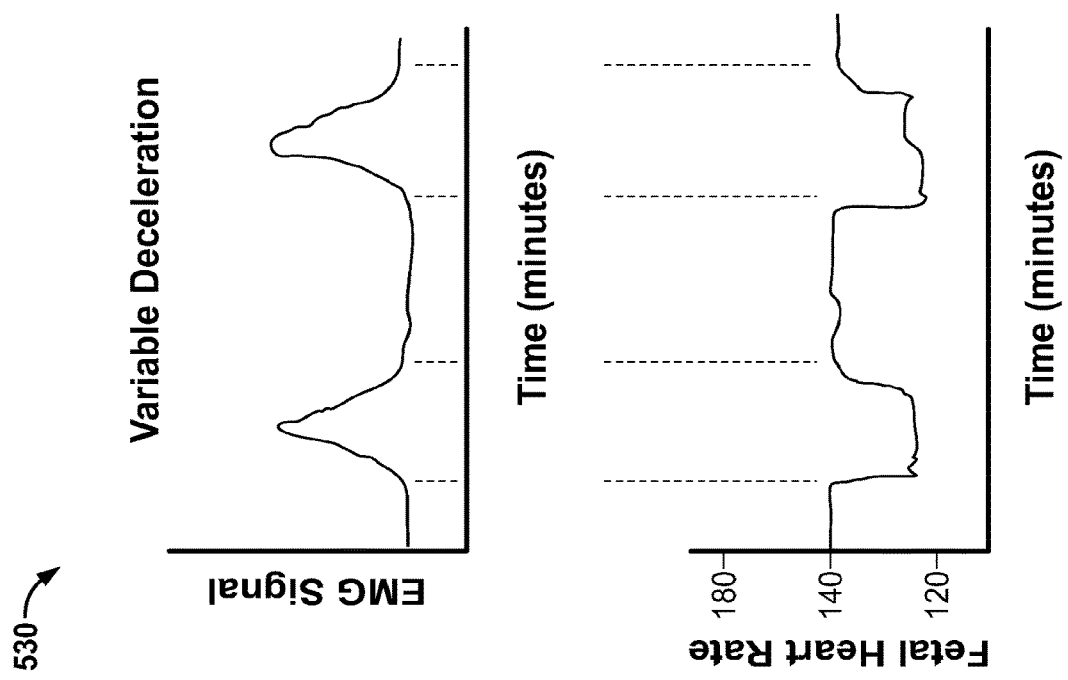

In other aspects, referring to FIG. 5, by combining fetal heart rate tracings with EMG contraction monitoring, a processor in the wearable device or in a remote device may infer even more detailed information about the fetus such as the overall health (in terms of blood flow through the umbilical cord) and the position. In alternative embodiments, a Doppler ultrasound sensor may be substituted for any one or any combination of the EMG or FHR sensors used for combined EMG and FHR monitoring.

If, for example, a processor detects acceleration in the fetal heart rate defined as having an onset to peak increase in less than some threshold 'A' seconds, for example 30 seconds, this state may be indicative of healthy fetal movements. Moreover, when healthy movements are detected, the device may be capable of analyzing this information and presenting it to the end user either via visual, audio, or tactile feedback.

If a processor detects, based on a FHR signal correlated to an EMG signal or other contraction signal, an Early Deceleration 510 in the fetal heart rate, wherein the fetal heart rate gradually drops at the onset of a contraction, with onset to nadir in greater than some threshold 'B' seconds, for example 30 seconds (wherein, 'B' is not necessarily equal to 'A'), and return to baseline that mirrors the uterine contraction, the processor may automatically interpret this signal condition as indicative of fetal head compression. Accordingly, the device may provide an output indication informing the mother that the head is vertex and her contractions are pressing on the child's head (which is normal and a reassuring sign).

If, based on the correlated signals a processor determines a Late Deceleration 520 exists in the fetal heart rate, wherein the fetal heart rate gradually drops after the onset of a contraction, with onset to nadir greater that some threshold of 'C' seconds, for example 30 seconds (wherein, 'C' is not necessarily equal to 'A' or 'B'), and returns to a baseline FHR after the uterine contraction returns to a rest state, the processor may automatically interpret this signal condition as indicative of fetal hypoxemia and insufficient delivery of blood to the placenta from the mother. Accordingly, the device may output a warning to the mother to seek medical attention.

If, based on the correlated signals a processor determines a Variable Deceleration 530 in the fetal heart rate, wherein the fetal heart rate abruptly drops at the onset of a contraction, with onset to nadir in then than some threshold 'D' seconds, for example 30 seconds (wherein, 'D' is not necessarily equal to 'A', 'B', or 'C', and lasting between predefined periods of 'E' and 'F' seconds respectively, for example 15 seconds to 120 seconds, the processor may automatically interpret this signal condition as suggestive of a umbilical cord compression, most often due to oligohydramnios. The device may then output a warning for the mother to seek medical attention right away.

If the end user desires, any of these events can selectively be sent to family members, friends, treating physician, the hospital, EMS, among others, as described herein above.

In another aspect, an algorithm for Fetal Surveillance User Interface based on protocols adapted from the obstetrics and gynecology literature may be performed by a processor unit based on input from an inertial sensor correlated in time to one or both of an EMG signal or FHR signal. In alternative embodiments, a Doppler ultrasound sensor may be substituted for any one or any combination of the inertial, EMG or FHR sensors. This interface may include, for example, a fetal movement assessment (FMA) protocol. Using an FMA protocol processing module and inertial sensor data, a wearable device with sensor processor or remote processor may provide a formal fetal movements assessment using the technology described. Over a one-hour time period, the mother may indicate on the wearable device or remote device every time she detects fetal movements, for example, using a touchscreen interface. The software will then calculate the number of movements recorded over each 20 minute time period. If there is an average of less than X number of fetal movements (for example 10) in Y number of minutes (for example 20 minutes), indicative of decreased fetal movements, the wearable device or a coupled remote device may warn the mother to perform a "Non-stress test" described below. In an alternative, using integrated inertial sensor such as, for example, an accelerometer or gyroscope, the wearable device may perform a fetal movement assessment automatically without any mother manual data input.

In a Non-Stress Test (NST) protocol, the device may provide an output instructing the mother via the user interface to lie in a lateral position. The wearable electronic device may then monitor the fetal heart rate and the EMG will measure uterine contractions. In some embodiments, a Doppler ultrasound sensor integrated into the wearable device may be used to monitor either or both of fetal heart rate and uterine contractions. The mother may be instructed to play music to provide acoustic stimulation. Various potential diagnoses may be based on fetal heart rate and contraction monitoring data.

For example, the processor may perform an algorithm to diagnose a Reactive Response (normal) from the FHR signal correlated in time to the EMG signal. The algorithm may define a normal reactive response, for example, as detection of some 'Z' number of accelerations, for example 2, of more than 'Q' fetal heart beats per minute, for example 15, above the baseline fetal heart rate for at least, 'R' seconds, for example 15 seconds, over an 'S' minute, for example 20 minute, time period.

For further example, the processor may perform an algorithm to diagnose a Nonreactive Response from the FHR signal correlated in time to the EMG signal. The algorithm may define a nonreactive response, for example, as detection of fewer than some 'Z' accelerations in 'S' minutes. Upon detecting this condition, the algorithm may cause the device to output a warning to consider going to the hospital to obtain further tests such as a biophysical profile. Lack of fetal heart rate accelerations may occur at gestational age less than 32 weeks, fetal sleeping, due to fetal brain anomalies, or maternal sedative administration.

In another aspect, a wearable sensor device in conjunction with a remote or local integrated processing unit may incorporate a prenatal diagnostic tests timeline in an application on the remote device and provide the end user with a set of warnings to indicate when various tests and OBGYN appointments are recommended during her pregnancy. This way, the end user is made aware of her recommended schedule according to her current gestational age.

For example, a prenatal diagnostic timeline module may process available data to provide a message informing the patient that Alpha fetoprotein may be attained at 15-20 weeks gestation and the purpose of the test, an amniocentesis is recommended at 15-17 weeks if the mother is more than 35 years old at the time of delivery. If conditions indicating an Rh-sensitized pregnancy, the device may inform the user to attain fetal blood type and related tests. In addition, while detecting a gestational age in a range of about 0-28 weeks, the device may output reminders to attend prenatal visits every 4 weeks, and at more frequent intervals later in gestation. For example, at about 29-36 weeks gestation, the device may output a reminder every 2 weeks to attend prenatal visits, and at 36 weeks gestation and beyond, the device may provide a reminder to attend parental visits weekly.

In another aspect, the device coupled with a processor and user interface may provide a user with calculators to calculate various changes that will take place during pregnancy. For example, Expected Weight Gain is 25-35 pounds for BMI 19.8-26 (less for obese women, and more for thinner women). The end user may be advised to add an additional 100-300 kcal/day in her diet during pregnancy. A calorie tracker based on food consumption may also be integrated into the device as well as an exercise tracker to aid in calculating net calories in and calories burned each day. A water tracker may also be integrated to ensure adequate hydration. The device may remind the user to take 0.4 mg/day of folic acid if no history of neural tube defects, and 4 mg/day if there is a history of neural tube defects, and may provide a recommendation to add iron supplementation with 325 mg iron sulfate during the latter half of pregnancy. The above are just examples of the many recommended treatments and/or decisions that may be displayed to the end user to aid in patient management of her pregnancy and allow the patient to be as informed as possible for her own health and that of her developing baby.

Figure 6:
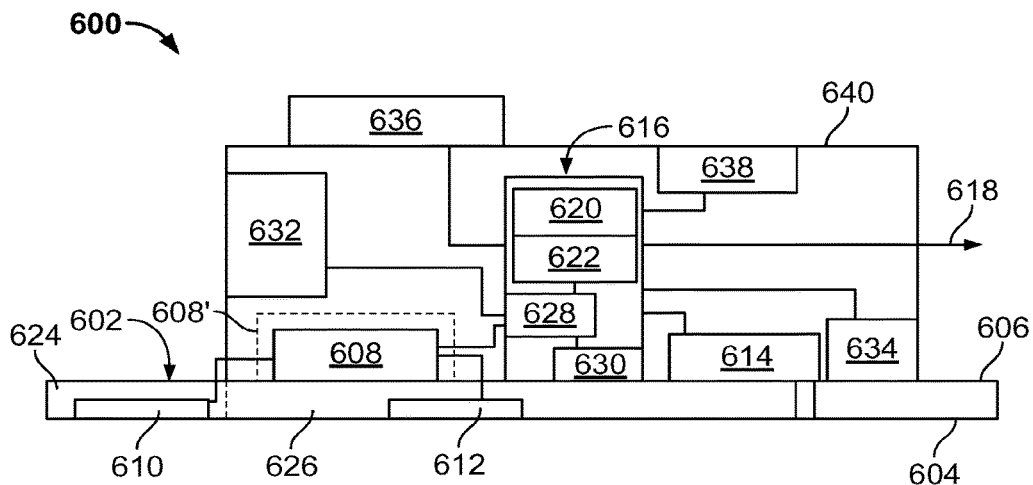
FIG. 6 illustrates a schematic diagram of an apparatus for automatically detecting a pregnancy status of a patient.

In summary of the foregoing, FIG. 6 illustrates a schematic diagram of an apparatus 600 for automatically detecting a pregnancy status of a patient. The apparatus may include a patch of material 602 having a proximal side 604 configured for adhering to human skin and a distal side 606 opposite to the proximal side. The apparatus 600 may further include an electromyography (EMG) sensor 608 directly or indirectly coupled to the patch of material 602, the EMG sensor comprising at least two electrodes 610, 612 disposed towards the proximal side 604 of the patch of material;

The apparatus 600 may further include a fetal heart rate (FHR) sensor 614 directly or indirectly coupled to the patch of material and configured for detecting a fetal heart rate signal when the proximal side 604 is adhered to skin of a patient. The FHR sensor may be selected from a Doppler ultrasound probe, an optical sensor providing output signal for photoplethysmography, or a set of electrodes arranged for providing an electrocardiographic (EKG) signal.

The apparatus 600 may further include an electronic circuit 616 directly or indirectly coupled to the patch of material, coupled to the EMG sensor and to the FHR sensor, and configured for providing an output 618 based on an EMG signal from the EMG sensor correlated in time to an FHR signal from the FHR sensor. Any suitable method of correlating signals from different sensors in time may be used, for example time stamping using a common clock or other time reference, combining signals, or other suitable method.

The electronic circuit may include a wireless transmitter 620 and the output 618 may include a wireless transmission of the EMG signal and FHR signal to a remote device. The electronic circuit may include a wireless receiver 622 configured for receiving a pregnancy status from the remote device based on the EMG signal and the FHR signal and the output 618 may further include a human-perceptible indication of the pregnancy status. For example, the output may include a visible indication on a display device, audible signal from an audio transducer, or tactile output from a vibrator or the like. The EMG sensor 608 and the FHR sensor 614 may share at least a portion of a sensor circuit, for example, these sensors may both be connected to and share use of a set of electrodes 610, 612. In alternative embodiments, one or both of the EMG sensor or FHR sensor may be replaced by a Doppler ultrasound sensor 608'. In such embodiments, an FHR signal or EMG signal may include indications of FHR or uterine contractions derived from Doppler analysis of ultrasonic input. Accordingly, such indications may be substituted for FHR signals and EMR signals as described elsewhere herein, in such embodiments. The Doppler ultrasound sensor may include an ultrasonic transducer/transmitter and a signal processor coupled to two or more spaced-apart ultrasonic receiver/microphones, and other components as known in the art.

In an aspect, the patch of material comprises separate pieces 624, 626, wherein each of the separate pieces 624, 626 includes at least one component coupled to the electronic circuit 616. The electronic circuit 616 may include a processor 628 coupled to a memory 630, the memory holding instructions that when executed by the processor 628 cause the electronic circuit to provide the output comprising an indication of a current pregnancy status based on the EMG signal and the FHR signal.

The apparatus 600 may further include an inertial sensor 632 directly or indirectly coupled to the patch of material 602 and configured for sensing fetal movement when the proximal side is adhered to skin of a patient. The electronic circuit 616 may be further configured to provide the output further based on an inertial motion signal from the inertial sensor 632. In an aspect, the apparatus 600 may optionally include any one of the EMG sensor 608 or FHR sensor 614, while omitting the other of these sensors.

The apparatus 600 may optionally include a temperature sensor 634, wherein the electronic circuit 616 is further configured to provide the output 618 further based on a temperature signal from the temperature sensor 634.

The apparatus 600 may further include an electronic display 636 coupled to the electronic circuit, the electronic display 636 configured for displaying an indication of a current pregnancy status based on the EMG signal and the FHR signal. For example, the display 636 may include one or more light-emitting diode (LED) indicator lights, alone or in conjunction with a liquid crystal display (LCD) panel. The apparatus 600 may further include an audio transducer 638 coupled to the electronic circuit, the audio transducer 638 configured for providing an audible indication of a current pregnancy status based on the EMG signal and the FHR signal. For example, the transducer 638 may include an audio speaker for emitting a tone or recorded message.

The apparatus 600 may further include a housing 640 enclosing the electronic circuit 616 and disposed on the distal side 606 of the patch of material 602. The electronic circuit 616 and all components within the housing 640 may be integrated into a thin, optionally flexible integrated circuit. It should be appreciated that the housing 640 is not drawn to scale, and in a production device may be much thinner relative to the patch than drawn. The patch 602 may be made of a pliable material, for example a flexible fabric or polymer membrane coated with a pressure-sensitive adhesive. The apparatus 600 and circuit 616 may include other components not shown, for example a battery or other power source, filters, diodes, logic gates, switches, ports, convertors, amplifiers and so forth, such as conventionally used in portable electronics.

Figure 7:
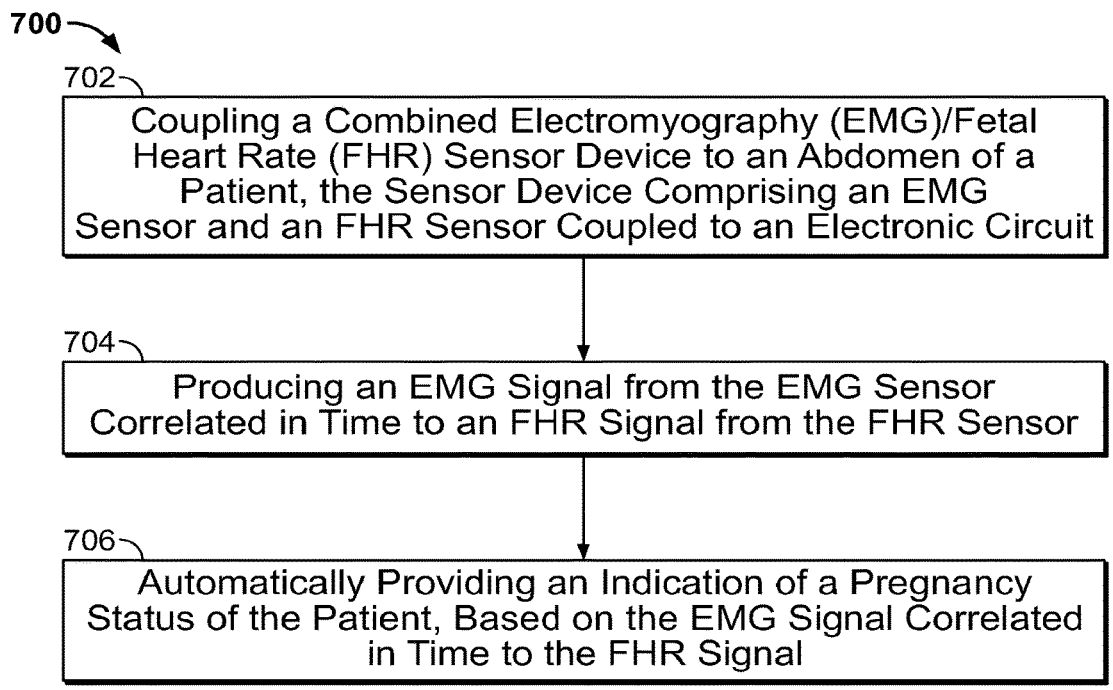
FIG. 7 is a flow chart illustrating aspects of a method for automatically detecting a pregnancy status of a patient, using an apparatus as shown in FIG. 6.

In another aspect with reference to FIG. 7, a method 700 for automatically detecting a pregnancy status of a patient may include, at 702, coupling (e.g., by adhering) a combined electromyography (EMG)/fetal heart rate (FHR) sensor device to an abdomen of a patient, the sensor device comprising an EMG sensor and an FHR sensor coupled to an electronic circuit. For example, any embodiment of the device 600 may be adhered to a patient abdomen. In alternative aspects, the sensor device may include an EMG sensor and inertial sensor while omitting an FHR sensor, or may include an FHR sensor and inertial sensor while omitting an EMG sensor or may use some other uterine contraction monitor instead of, or in addition to, the EMG sensor.

The method 700 may further include, at 704, producing an EMG signal from the EMG sensor correlated in time to an FHR signal from the FHR sensor. For example, a signal processor may receive data from two or more sensors as described herein, and output separate data streams associated with a common timeline, or a combined data stream including information from both sensors on a common timeline. The FHR sensor may be selected from, for example, a Doppler ultrasound probe, an optical sensor providing a photoplethysmographic signal, and a set of electrodes providing an electrocardiographic (EKG) signal. In an alternative aspect, the method may include (instead of or in addition to block 704) producing an EMG signal from the EMG sensor correlated in time to a fetal movement signal from an inertial sensor, or producing an FHR signal from the FHR sensor correlated in time to a fetal movement signal from the inertial sensor.

The method 700 may further include, at 706, automatically providing an indication of a pregnancy status of the patient, based on the EMG signal correlated in time to the FHR signal. In alternative or additional aspects, the indication of pregnancy status may be automatically provided based on the EMG signal correlated in time to the fetal movement signal, or on the FHR signal correlated in time to the fetal movement signal. More detailed aspects and algorithms for providing the indication of pregnancy status are described above, with selected (but not all) algorithms summarized in the discussion below.

In additional aspects, the method 700 may include wirelessly transmitting the EMG signal and FHR signal to a remote device. In such aspects, the method may further include receiving the pregnancy status from the remote device, and outputting the indication of the pregnancy status from at least one of a display device or a transducer in a human-perceptible form (e.g., display, sound, or tactile signal).

In other additional aspects, the method 700 may include processing the EMG signal correlated in time to the FHR signal using a processor located in the combined EMG/FHR sensor device, thereby obtaining the indication of the pregnancy status. In the alternative, or in addition, the method may include processing the EMG signal correlated in time to the FHR signal using a processor located in a remote device, thereby obtaining the indication of the pregnancy status. The method 700 may also include outputting the indication of the pregnancy status from the remote device, wherein the remote device comprises at least one of a smartphone or a tablet computer.

In another aspect of the method 700, the combined EMG/FHR sensor device may further include a temperature sensor, and the method may further include providing the indication of the pregnancy status further based on a temperature signal from the temperature sensor.

In an aspect of the method 700, providing the indication of the pregnancy status may include providing an indication of onset of labor based on an intensity, duration and rate of contractions detected by the EMG sensor. In another aspect, providing the indication of the pregnancy status may include providing an indication of fetal distress during labor based on a FHR detected by the FHR sensor, or based on the EMG signal correlated in time to the FHR signal.

As disclosed in more detail above, the method 700 may further include providing the indication of the pregnancy status indicating a normal status based on detecting an acceleration of FHR for a period less than a defined time threshold correlated to sensor input indicating fetal movement. In addition, the method 700 may further include providing the indication of the pregnancy status indicating a normal status based on detecting an early deceleration in the FHR that occurs gradually from the onset of a contraction for a period less than a defined time threshold and that returns to a baseline FHR after the contraction. For further example, the method 700 may also include providing the indication of the pregnancy status indicating a fetal hypoxemia status based on detecting a late deceleration wherein the FHR gradually drops after onset of the contraction for a period greater than a defined time threshold and that returns to a baseline FHR after the contraction. In addition, the method may further include providing the indication of the pregnancy status indicating an umbilical cord compression status based on detecting a variable deceleration in the FHR wherein the FHR abruptly drops at the onset of a contraction over a period less than a defined time threshold and remains depressed for a second period greater than a second defined time threshold. In any or all cases, the method 700 may further include accompanying the indicating of the fetal hypoxemia status with a warning advising medical attention. Other status-determining algorithms based on different sensor data may be included in the method 700 or in similar methods, based on the detailed examples provided earlier in the specification.

Figure 8:
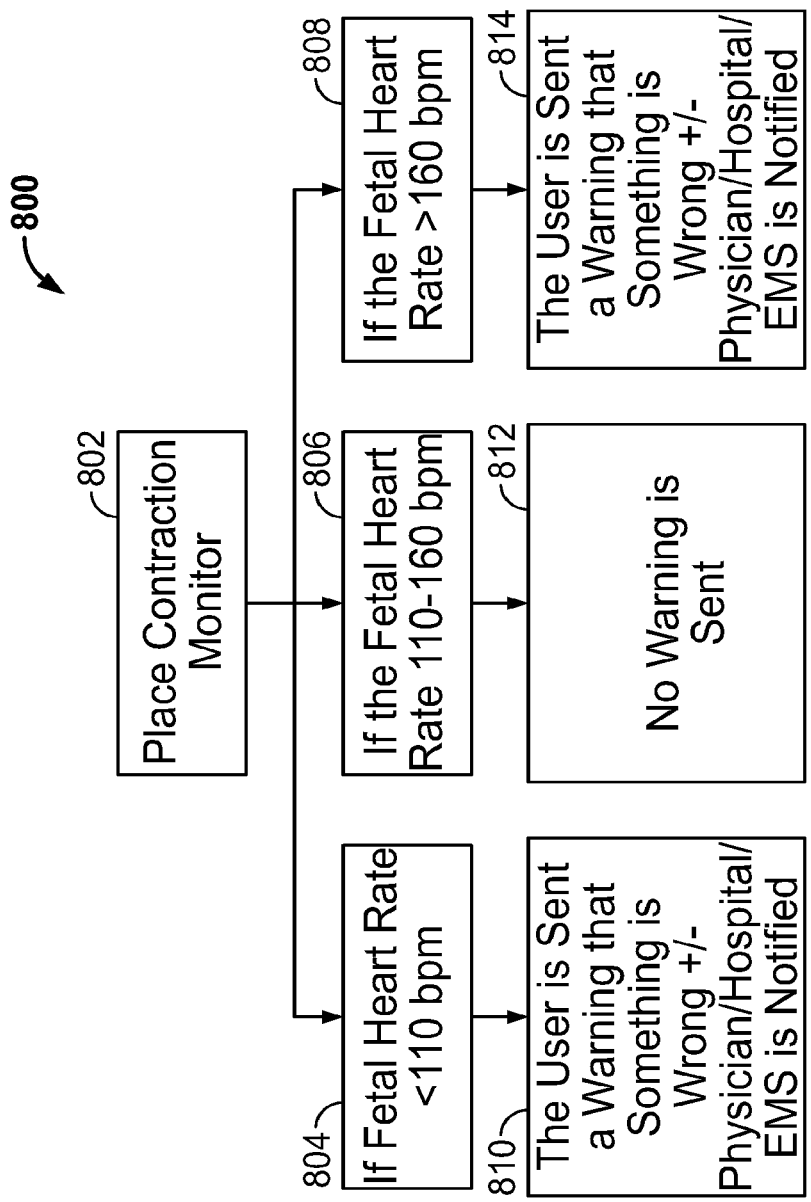
FIGS. 8 and 9 are flow charts showing examples of diagnostic methods that may be performed using a wearable sensing device.

FIG. 8 shows an alternative state diagram view of an algorithm 800 similar to the algorithm 300 discussed in connection with FIG. 3, but concerned with fetal health monitoring. At 802, a contraction and FHR monitor is placed on the patient. The algorithm 800 may be performed independently during or before contraction monitoring. At state 804, the algorithm determines that the fetal heart rate is less than a medically relevant threshold, for example, 110 beats per minute. Based on this determination, the algorithm causes a warning message to be displayed at 810, and/or transmits a warning message to one or more addresses designated for the patient, patient's physician, hospital or emergency response service. At state 806, the algorithm determines that the fetal heart rate is within a medically relevant range, for example 110 to 160 beats per minute, that does not indicate fetal distress. Accordingly, monitoring may be continued and as indicated at 812, no warning is sent. At state 808, the algorithm determines that the fetal heart rate is greater than a medically relevant threshold, for example, 160 beats per minute. Based on this determination, the algorithm causes a warning message to be displayed at 814, and/or transmits a warning message to one or more addresses designated for the patient, patient's physician, hospital or emergency response service.

Figure 9:
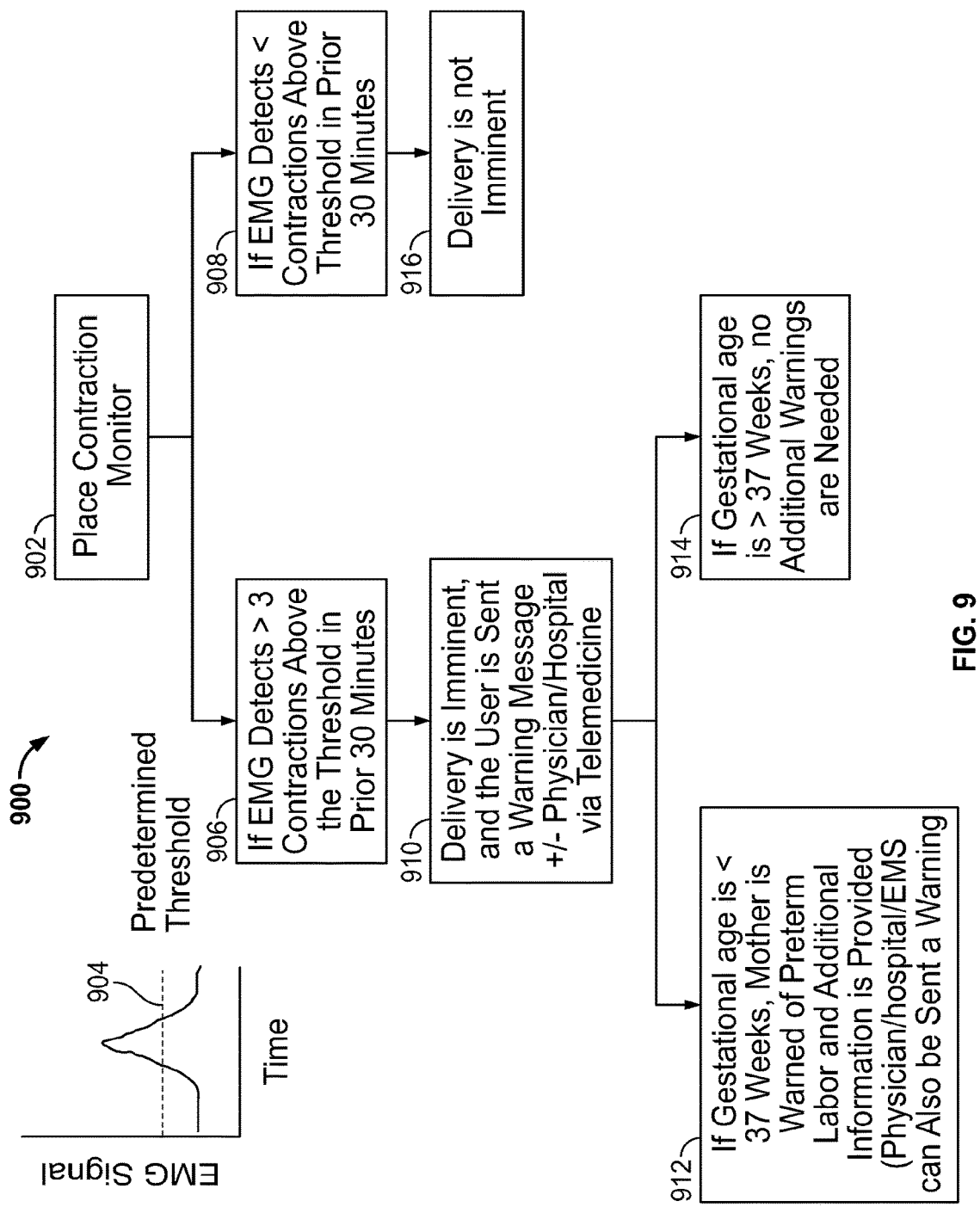

FIG. 9 shows an alternative view of an algorithm 900 similar to the algorithm 300 discussed in connection with FIG. 3 for contraction monitoring, in the form of a state diagram. At 902, a contraction monitor is placed on the patient. The algorithm 900 may be performed independently during fetal heart rate monitoring. At state 906, the algorithm determines a certain number (for example, at least three) of contractions that measure as stronger than a medically relevant, non-zero threshold 904 within a defined time period, for example, thirty minutes. Based on this determination, the algorithm determines that delivery is imminent, and causes a warning message to be displayed at 910, and/or transmits a warning message to one or more addresses designated for the patient, patient's physician, hospital or emergency response service. The content of the warning message may be determined based on the measured gestational age. For example, if the algorithm determines that the gestational age is less than a medically relevant threshold (e.g., 37 weeks), the warning message may include an indication of pre-term delivery as indicated at 912. Conversely, if the algorithm determines that the gestational age is greater than the medically relevant threshold, the warning message may include an indication of term delivery or not additional indications as shown at 914. At state 908, the algorithm determines that the number of contractions above the threshold 904 does not exceed the trigger amount (e.g., three) within the predetermined period (e.g., the most recent thirty minutes). Accordingly, monitoring may be continued while delivery is not determined to be imminent as indicated at 916, and no warning is sent.

In one or more exemplary designs, control functions of the described fetal monitoring device, for example signal processing and output algorithms, may be implemented in hardware, software, firmware, or any combination thereof. If implemented in software, the functions may be stored as one or more instructions or code on a non-transitory computer-readable medium. Computer-readable media includes computer storage media or any other non-transitory tangible medium that facilitates holding a computer program in storage or machine memory. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Combinations of the above should also be included within the scope of computer-readable media.

Accordingly, a system, method and apparatus for a fetal monitoring using a combined EMG (or other uterine contraction monitor) and FHR sensor or inertial sensor are disclosed. The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but should be accorded the widest scope consistent with the principles and novel features disclosed herein.

What is claimed is:
1. An apparatus for automatically detecting a pregnancy status of a patient, the apparatus comprising:
  a patch of material having a proximal side configured for adhering to human skin and a distal side opposite to the proximal side;

a uterine contraction monitor coupled to the patch of material and configured for sensing uterine contractions when the proximal side is adhered to skin of a patient;

a fetal heart rate (FHR) sensor coupled to the patch of material and configured for detecting a FHR signal when the proximal side is adhered to skin of the patient; and an electronic circuit coupled to the patch of material, the uterine contraction monitor, and the FHR sensor, the electronic circuit comprising a processor, wherein the apparatus is configured to:

detect contractions from a signal received from the uterine contraction monitor;

analyze a strength, a duration, and a frequency of the contractions;

detect an FHR from the FHR signal received from the FHR sensor;

determine whether there is an early deceleration, a late deceleration, an acceleration, a variable deceleration, or a change in the FHR signal;

correlate, based on time, the signal from the uterine contraction monitor to the FHR signal from the FHR sensor; and automatically output to the patient an indication of a pregnancy status and one or more of fetal movement, normal fetal status, and fetal distress based on said correlation.

2. The apparatus of claim 1, wherein the electronic circuit comprises a wireless transmitter for wirelessly transmitting signals to a remote device.

3. The apparatus of claim 2, wherein the electronic circuit comprises a wireless receiver configured for receiving the pregnancy status from the remote device.

4. The apparatus of claim 1, wherein the patch of material comprises separate pieces, wherein each of the separate pieces includes at least one component coupled to the electronic circuit.

5. The apparatus of claim 1, wherein the processor is coupled to a memory, the memory holding instructions that when executed by the processor cause the electronic circuit to analyze the detected contractions.

6. The apparatus of claim 1, further comprising an inertial sensor coupled to the patch of material and configured for sensing fetal movement when the proximal side is adhered to skin of the patient.

7. The apparatus of claim 6, wherein the processor is further configured to provide an output based on an inertial motion signal from the inertial sensor.

8. The apparatus of claim 1, further comprising a temperature sensor, wherein the processor is further configured to provide an output based on a temperature signal from the temperature sensor.

9. The apparatus of claim 1, wherein the FHR sensor is selected from: a Doppler ultrasound probe, an optical sensor providing output signal for photoplethysmography, and a set of electrodes arranged for providing an electrocardiographic (EKG) signal.

10. The apparatus of claim 1, further comprising a housing enclosing the electronic circuit and disposed on the distal side of the patch of material.

11. The apparatus of claim 1, further comprising an electronic display coupled to the electronic circuit, the electronic display configured for displaying an indication of a current pregnancy status.

12. The apparatus of claim 1, further comprising an audio transducer coupled to the electronic circuit, the audio transducer configured for providing an audible indication of a current pregnancy status.

13. The apparatus of claim 1, wherein the patch is comprised of a pliable material.

14. The apparatus of claim 9, wherein one or both of the uterine contraction monitor and the FHR sensor comprise a Doppler ultrasound sensor.

15. A method for automatically detecting a pregnancy status of a patient, the method comprising:

coupling an apparatus to an abdomen of a patient, the apparatus comprising a patch of material, a uterine contraction monitor coupled to the patch of material, a fetal heart rate (FHR) sensor coupled to the patch of material, and an electronic circuit coupled to the patch of material, wherein the apparatus further comprises a processor, and wherein the apparatus is configured to:

detect contractions from a signal received from the uterine contraction monitor;

analyze a strength, a duration, and a frequency of the contractions;

detect an FHR from an FHR signal received from the FHR sensor;

determine whether there is an early deceleration, a late deceleration, an acceleration, a variable deceleration, or a change in the FHR signal;

correlate, based on time, the signal from the uterine contraction monitor to the FHR signal from the FHR sensor; and automatically output to the patient an indication of a pregnancy status and one or more of fetal movement, normal fetal status, and fetal distress based on said correlation.

16. The method of claim 15, wherein the apparatus is further configured to wirelessly transmit signals to a remote device.

17. The method of claim 16, wherein the apparatus is further configured to receive the pregnancy status from the remote device, and output the indication of the pregnancy status from at least one of a display device or a transducer in a human-perceptible form.

18. The method of claim 15, wherein analyzing the strength, the duration, and the frequency is performed using the processor coupled to the electronic circuit.

19. The method of claim 15, wherein analyzing the strength, the duration, and the frequency is performed using a second processor located in a remote device.

20. The method of claim 19, wherein the apparatus is further configured to output the indication of the pregnancy status from the remote device.

21. The method of claim 20, wherein the remote device comprises at least one of a smartphone or a tablet computer.

22. The method of claim 15, wherein the patch further comprises an inertial sensor configured for sensing fetal movement, and the method further comprises providing an indication of the pregnancy status further based on an inertial motion signal from the inertial sensor.

23. The method of claim 15, wherein the patch further comprises an inertial sensor configured for sensing fetal movement, and the apparatus is further configured to provide a separate indication of the pregnancy status based on an inertial motion signal from the inertial sensor excluding the signal received from the uterine contraction monitor.

24. The method of claim 15, wherein the patch further comprises a temperature sensor, and the apparatus is further configured to provide the indication of the pregnancy status further based on a temperature signal from the temperature sensor.

25. The method of claim 15, wherein the FHR sensor is selected from: a Doppler ultrasound probe, an optical sensor providing a photoplethysmographic signal, and a set of electrodes providing an electrocardiographic (EKG) signal.

26. The method of claim 15, wherein the apparatus is further configured to provide an indication of onset of labor based on an intensity the strength, the duration and the frequency of contractions detected by the uterine contraction monitor.

27. The method of claim 15, wherein the apparatus is further configured to indicate the normal fetal status based on detecting the acceleration of the FHR for a period less than a defined time threshold correlated to a sensor input indicating fetal movement.

28. The method of claim 15, wherein the early deceleration in the FHR signal occurs gradually from an onset of the contraction for a period less than a defined time threshold and returns to a baseline FHR after the contraction, indicating the normal fetal status.

29. The method of claim 15, wherein the apparatus is further configured to indicate a fetal hypoxemia status based on detecting the late deceleration wherein the FHR signal gradually drops after onset of the contraction for a period greater than a defined time threshold and that returns to a baseline FHR after the contraction.

30. The method of claim 29, further comprising accompanying the indication of the fetal hypoxemia status with a warning advising medical attention.

31. The method of claim 15, wherein the apparatus is further configured to indicate an umbilical cord compression status based on detecting the variable deceleration in the FHR signal wherein the FHR signal abruptly drops at an onset of the contraction over a period less than a defined time threshold and remains depressed for a second period greater than a second defined time threshold.

32. The method of claim 15, wherein one or both of the uterine contraction monitor and the FHR sensor comprise a Doppler ultrasound sensor.

33. An apparatus for automatically detecting a pregnancy status of a patient, the apparatus comprising:
a patch of material having a proximal side configured for adhering to human skin and a distal side opposite to the proximal side;
an electromyography (EMG) sensor coupled to the patch of material, the EMG sensor comprising at least two electrodes disposed toward the proximal side of the patch of material and configured for sensing uterine contractions when the proximal side is adhered to skin of a patient;
a fetal heart rate (FHR) sensor coupled to the patch of material and configured for detecting an FHR signal when the proximal side is adhered to skin of the patient; and
an electronic circuit coupled to the patch of material, the EMG sensor, and the FHR sensor, the electronic circuit comprising a processor, wherein the apparatus is configured to:
detect contractions from a signal received from the EMG sensor;
analyze a strength, a duration, and a frequency of the contractions;
detect an FHR from the FHR signal received from the FHR sensor;
determine whether there is an early deceleration, a late deceleration, an acceleration, a variable deceleration, or a change in the FHR signal;
correlate, based on time, the signal from the EMG sensor to the FHR signal from the FHR sensor; and
automatically output to the patient an indication of a pregnancy status and one or more of fetal movement, normal fetal status, and fetal distress based on said correlation.

34. The apparatus of claim 33, wherein the electronic circuit comprises a wireless transmitter for wirelessly transmitting signals to a remote device.

35. The apparatus of claim 34, wherein the electronic circuit comprises a wireless receiver configured for receiving the pregnancy status from the remote device.

36. The apparatus of claim 33, wherein the patch of material comprises separate pieces, wherein each of the separate pieces includes at least one component coupled to the electronic circuit.

37. The apparatus of claim 33, wherein the processor is coupled to a memory, the memory holding instructions that when executed by the processor cause the processor to analyze the detected contractions.

38. The apparatus of claim 33, further comprising a temperature sensor, wherein the processor is further configured to provide an output further based on a temperature signal from the temperature sensor.

39. The apparatus of claim 33, further comprising an inertial sensor, wherein the inertial sensor is selected from: a Doppler ultrasound probe, an optical sensor providing output signal for photoplethysmography, and a set of electrodes arranged for providing an electrocardiographic (EKG) signal.

40. The apparatus of claim 33, further comprising a housing enclosing the electronic circuit and disposed on the distal side of the patch of material.

41. The apparatus of claim 33, further comprising an electronic display coupled to the electronic circuit, the electronic display configured for displaying an indication of a current pregnancy status.

42. The apparatus of claim 33, further comprising an audio transducer coupled to the electronic circuit, the audio transducer configured for providing an audible indication of a current pregnancy status.

43. The apparatus of claim 33, wherein the patch is comprised of a pliable material.

44. A method for automatically detecting a pregnancy status of a patient, the method comprising:
coupling, to an abdomen of a patient, an apparatus comprising a patch of material, an electromyography (EMG) sensor, a fetal heart rate (FHR) sensor, and an electronic circuit coupled to the patch of material and comprising a processor, wherein the apparatus is configured to:
detect contractions from an EMG signal received from the EMG sensor;
analyze a strength, a duration, and a frequency of the contractions;
detect an FHR from an FHR signal received from the FHR sensor;
determine whether there is an early deceleration, a late deceleration, an acceleration, a variable deceleration, or a change in the FHR signal;
correlate, based on time, the EMG signal from the EMG sensor to the FHR signal from the FHR sensor; and automatically output to the patient an indication of a pregnancy status and one or more of fetal movement, normal fetal status, and fetal distress based on said correlation.

45. The method of claim 44, further comprising wirelessly transmitting signals to a remote device.

46. The method of claim 45, further comprising receiving the pregnancy status from the remote device, and outputting the indication of the pregnancy status from at least one of a display device or a transducer in a human-perceptible form.

47. The method of claim 44, wherein analyzing the strength, the duration, and the frequency is performed using the processor coupled to the patch.

48. The method of claim 44, wherein analyzing the strength, the duration, and the frequency is performed using a second processor located in a remote device.

49. The method of claim 48, further comprising outputting the indication of the pregnancy status from the remote device.

50. The method of claim 48, wherein the remote device comprises at least one of a smartphone or a tablet computer.

51. The method of claim 44, wherein the apparatus further comprises a temperature sensor, and the apparatus is further configured to provide the indication of the pregnancy status further based on a temperature signal from the temperature sensor.

52. An apparatus for automatically detecting a pregnancy status of a patient, the apparatus comprising:
 a patch of material having a proximal side configured for adhering to human skin and a distal side opposite to the proximal side;
 a Doppler ultrasound sensor coupled to the patch of material, configured for sensing a fetal heart rate (FHR) and uterine contractions when the proximal side is adhered to skin of a patient; and
 an electronic circuit coupled to the patch of material and the Doppler ultrasound sensor, wherein the electronic circuit comprises a processor configured to:
  detect contractions from a contraction signal received from the Doppler ultrasound sensor,
  analyze a strength, a duration, and a frequency of the contractions,
  detect the FHR from an FHR signal received from the Doppler ultrasound sensor,
  determine whether there is an early deceleration, a late deceleration, an acceleration, a variable deceleration, or a change in the FHR signal,
  correlate, based on time, the contraction signal to the FHR signal from the FHR sensor Doppler ultrasound sensor, and
  automatically output to the patient an indication of a pregnancy status and one or more of fetal movement, normal fetal status, and fetal distress based on said correlation.

53. The apparatus of claim 52, wherein the electronic circuit comprises a wireless transmitter and the processor is further configured to wirelessly transmit signals to a remote device.

54. The apparatus of claim 53, wherein the electronic circuit comprises a wireless receiver configured to receive the pregnancy status from the remote device.

55. An apparatus for automatically detecting a pregnancy status of a patient, the apparatus comprising:
 a patch of material having a proximal side configured for adhering to human skin and a distal side opposite to the proximal side;
 a wearable biosensor coupled to the patch of material, configured for sensing uterine contractions and fetal heart rate (FHR) when the proximal side is adhered to skin of a patient; and
 an electronic circuit coupled to the patch of material and the wearable biosensor, wherein the electronic circuit comprises a processor configured to:
  detect contractions from a contraction signal received from the wearable biosensor,
  analyze a strength, a duration, and a frequency of the contractions,
  detect the FHR from an FHR signal received from the wearable biosensor,
  determine whether there is an early deceleration, a late deceleration, an acceleration, a variable deceleration, or a change in the FHR signal,
  correlate, based on time, the contraction signal to the FHR signal from the wearable biosensor, and
  automatically output to the patient an indication of a pregnancy status and one or more of fetal movement, normal fetal status, and fetal distress based on said correlation.

56. The apparatus of claim 55, wherein the electronic circuit comprises a wireless transmitter and the processor is configured to wirelessly transmit signals to a remote device.

57. The apparatus of claim 56, wherein the electronic circuit comprises a wireless receiver configured to receive the pregnancy status from the remote device.

58. The apparatus of claim 1, wherein said correlating comprises correlating, based on time, the frequency of the contractions to the FHR signal from the FHR sensor.

59. The method of claim 15, wherein the apparatus is further configured to:
 detect the early deceleration in the FHR, wherein the early deceleration comprises a gradual drop at an onset of the contraction, with onset to nadir for a period greater than a defined time threshold, and a return to baseline that mirrors the contraction; and
 output the normal fetal status indicating that a fetal head is vertex.

* * * * *

UNITED STATES PATENT AND TRADEMARK OFFICE
CERTIFICATE OF CORRECTION

PATENT NO. : 10,278,581 B2
APPLICATION NO. : 14/909739
DATED : May 7, 2019
INVENTOR(S) : Richard S. Gaster Page 1 of 1

It is certified that error appears in the above-identified patent and that said Letters Patent is hereby corrected as shown below:

In the Claims

In Claim 26, Column 19, Line 10, "an intensity" should be deleted

In Claim 52, Column 21, Line 49, "FHR sensor" should be deleted

Signed and Sealed this
Second Day of July, 2019

Andrei Iancu
*Director of the United States Patent and Trademark Office*